(12) United States Patent
Hall

(10) Patent No.: US 8,788,022 B2
(45) Date of Patent: Jul. 22, 2014

(54) N-TIME-GATE DATA-TYPE FOR TPSF-BASED OPTICAL IMAGING

(75) Inventor: David Jonathan Hall, Montréal (CA)

(73) Assignee: President and Fellows of Harvard College, Cambridge, MA (US)

(*) Notice: Subject to any disclaimer, the term of this patent is extended or adjusted under 35 U.S.C. 154(b) by 1741 days.

(21) Appl. No.: 10/757,937

(22) Filed: Jan. 16, 2004

(65) Prior Publication Data

US 2004/0147844 A1 Jul. 29, 2004

Related U.S. Application Data

(60) Provisional application No. 60/305,081, filed on Jul. 16, 2001.

(30) Foreign Application Priority Data

Jul. 16, 2002 (WO) .................. PCT/CA02/01067
Jan. 22, 2003 (WO) .................. PCT/CA03/00047

(51) Int. Cl.
*A61B 6/00* (2006.01)

(52) U.S. Cl.
USPC .............. 600/476; 359/11; 359/237; 359/238

(58) Field of Classification Search
USPC .................................. 250/206; 600/425, 476
See application file for complete search history.

(56) References Cited

U.S. PATENT DOCUMENTS

| | | | |
|---|---|---|---|
| 4,958,231 A | 9/1990 | Tsuchiya | 358/211 |
| 5,371,368 A | 12/1994 | Alfano et al. | 250/341.1 |
| 5,692,511 A * | 12/1997 | Grable | 600/425 |
| 5,987,351 A * | 11/1999 | Chance | 600/473 |
| 6,070,583 A * | 6/2000 | Perelman et al. | 600/476 |
| 6,339,216 B1 * | 1/2002 | Wake | 250/214 A |
| 6,509,729 B2 * | 1/2003 | Levitt | 324/76.36 |
| 6,736,321 B2 * | 5/2004 | Tsikos et al. | 235/462.14 |
| 7,231,243 B2 * | 6/2007 | Tearney et al. | 600/407 |
| 2002/0067901 A1 * | 6/2002 | Mukherjee et al. | 385/116 |
| 2002/0100864 A1 * | 8/2002 | Wake | 250/208.1 |
| 2002/0177778 A1 * | 11/2002 | Averback et al. | 600/476 |
| 2003/0007134 A1 * | 1/2003 | Maximus | 353/31 |

FOREIGN PATENT DOCUMENTS

WO WO 99/27343 6/1999
WO WO 00/46979 8/2000

OTHER PUBLICATIONS

Kwong et al., "400-Hz mechanical scanning optical delay line", 1993, Optics Letters, vol. 18, No. 7, pp. 558-560.*
American Institute of Physics, Schmidt, Florian E.W. et al., *A 32-Channel Time-Resolved Instrument for Medical Optical Tomography*, , Review of Scientific Instruments, vol. 71, No. 1, Jan. 2000, pp. 256-265.

* cited by examiner

*Primary Examiner* — Unsu Jung
*Assistant Examiner* — Shahdeep Mohammed
(74) *Attorney, Agent, or Firm* — McCarter & English, LLP

(57) ABSTRACT

There is provided a method and system for optical imaging of a light scattering object. The method comprises the detection of one or more time-gates of a temporal point spread function (TPSF) to be used to construct an image of optical properties of the object. The method also comprises the simultaneous detection of two or more selected time-gates using a time-gated camera. The method enables more efficient spatial-temporal acquisition of optical signals for imaging purposes.

24 Claims, 5 Drawing Sheets

N-TIME-GATE DATA-TYPE FOR TPSF-BASED OPTICAL IMAGING

CROSS-REFERENCE TO RELATED APPLICATIONS

This application is a Continuation-In-Part Application of PCT/CA02/01067, filed Jul. 16, 2002, designating the United States, now pending and claims priority right under 35 U.S.C. 119(e) of U.S. Provisional Patent Application Ser. No. 60/305,081 filed Jul. 16, 2001. This application is also a Continuation of PCT/CA03/00047, filed Jan. 22, 2003, designating the United States, now pending. The specifications of said applications are hereby incorporated by reference.

MICROFICHE APPENDIX

Not applicable.

TECHNICAL FIELD

This invention relates to the field of temporal point spread function (TPSF) based imaging in which objects which diffuse light, such as some human body tissues, are imaged using signals resulting from the injection of light into the object and detection of the diffusion of the light in the object at a number of positions while gathering TPSF-based data to obtain information beyond simple attenuation such as scattering and absorption. More particularly, the present invention relates to a specific data-type, N-time-gate, which can be obtained from TPSF-based data.

BACKGROUND OF THE INVENTION

Time-domain optical medical imaging shows great promise as a technique for imaging breast tissue, as well as the brain and other body parts. The principle of the technique lies in the analysis of the temporal point spread function (TPSF) of an injected pulse of light which is diffused in an object of interest (OOI), and in the extraction of information from the TPSF to construct a medically useful image. The (complete) TPSF is defined as the light intensity of a given wavelength presented as a function of time t ($t_o \leq t \leq \infty$) that can be observed at a given spatial location after a very short pulse of light produced at another spatial location at the time $t_o$.

Specific types of data extracted from the TPSF are known as 'Data-types'. For example, 'early time-gated attenuation' is a Data-type that can be extracted from the TPSF which improves the image spatial resolution over continuous wave methods. However, it is unclear whether such improvements in image spatial resolution are adequate for diagnosing certain diseases, such as breast cancer, based on morphology.

An alternative approach is to use the TPSF to decouple the light attenuation into absorption and scattering components. This extra information, which generally cannot be obtained with continuous wave methods, may be clinically useful. In order to achieve this it is customary to extract appropriate Data-types from the TPSF. Researchers, in the time-domain field, have looked at data-types such as the meantime and higher moments of the TPSF (Arridge, 1999). Whilst data-types for optical data acquired in the frequency domain have included phase-shift and amplitude.

There are several techniques for measuring the TPSF arising from a light pulse that has traveled through an OOI such as breast tissue. Certainly the most information one can acquire is by measuring a complete TPSF. This information can also be acquired in the frequency domain, although current hardware limitations mean that time-domain hardware is capable of acquiring information over a larger bandwidth than its frequency domain counterpart.

However, acquiring a practical approximation f(t), t∈[a,b] to the complete TPSF, such that $$\int_a^b f(t)\,dt \approx \int_{t_0}^{\infty} f(t)\,dt,$$

has implications in terms of long acquisition times for clinical systems, and possibly unacceptably long data-processing for image reconstruction algorithms.

It would therefore be desirable to provide methods overcoming the limitations of the prior art.

SUMMARY OF THE INVENTION

For the purpose of image construction, the entire TPSF derived from a pulse of light can be used. The streak camera has commonly been used for this purpose. However the detection surface of a streak camera may be limited. Time-gated cameras such as intensified charge coupled device (ICCD) typically have greater detection surface areas but acquisition of complete TPSFs using such camera may be time consuming.

It is therefore an object of the present invention to provide a method and apparatus for TPSF-based imaging of an object in which acquisition times are reduced while still extracting a sufficient amount of desired information from the TPSF of a collected optical signal to be used in producing an optical image.

According to a broad aspect of the invention this objective is achieved by detecting selected intervals, or N-time-gates, of a TPSF. The detection of the selected time-gates is effected using time-gated detection techniques and cameras.

In a further aspect of the invention, the acquisition time is substantially reduced by simultaneously detecting selected time gates of a TPSF.

Thus in one aspect of the present invention there is provided a method for simultaneously detecting N-time-gates Data-type of a TPSF of a collected optical signal, the method comprising pulsing the object with a light pulse delivered at one or more injection ports, collecting a plurality of optical signals based TPSF's at collection ports, introducing delays in propagation of the optical signals to produce staggered TPSF's and simultaneously detecting selected time-gates.

In an embodiment of the invention the delays in the propagation of the optical signals are provided by using optical fibers of different lengths to collect the optical signals.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

In accordance with the present invention, there is provided a method and apparatus using a N-time-gate Data-Type for TPSF-based optical imaging.

Figure 1:
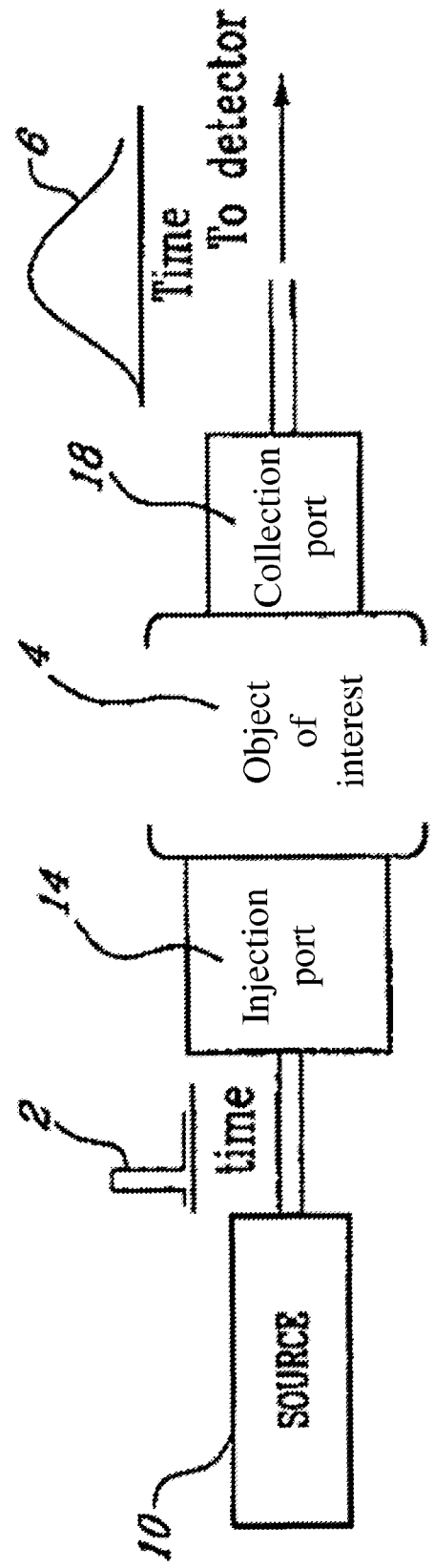
FIG. 1 is a diagram showing an embodiment of the system used to generate a pulse of light and to produce a TPSF after injection of the light in an object.

FIG. 1 schematically represents the events giving rise to a TPSF. A pulse of light 2 is generated at a source 10 and injected in an OOI 4 at injection port 14. The OOI may be a body part such as a breast but it will be appreciated that the method and apparatus described herein can be applied to any suitable object. The light interacts with the medium by being absorbed and/or scattered and exits the OOI with an attenuated intensity. The exiting attenuated light can be collected at collection port 18 as a function of time to produce the TPSF 6. The shape of the TPSF depends on the type of interactions that occurred between the light and the medium. Images (maps of optical properties) may be constructed by extracting appropriate Data-types from the TPSF and by inputting them to an appropriate image reconstruction algorithm, i.e. one which forward models the data and solves the appropriate inverse problem.

Figure 2:
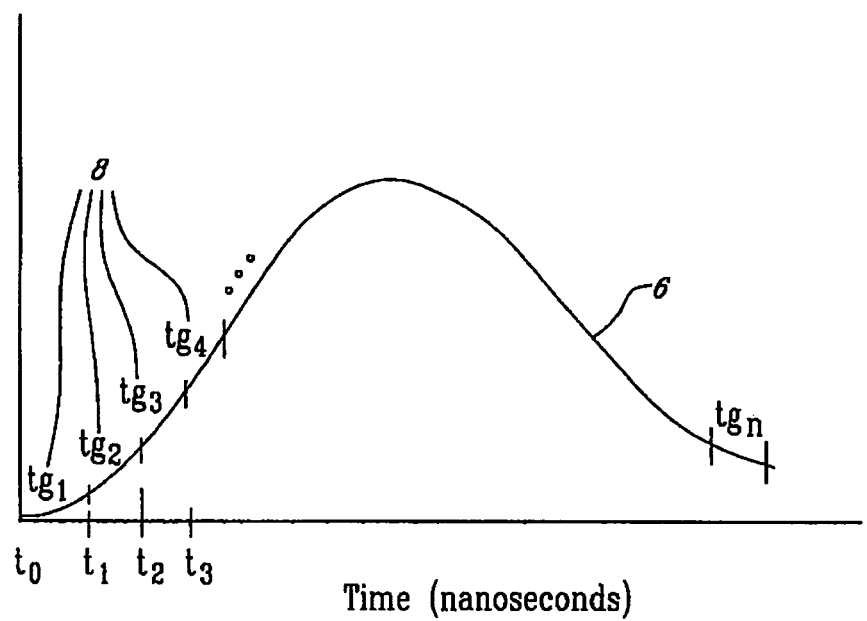
FIG. 2 is a graphical representation of a TPSF showing arbitrarily defined time-gates.

In one embodiment, the present invention provides a method for detecting only selected intervals of a TPSF. In FIG. 2 it can be seen that a TPSF can be subdivided in n arbitrary intervals 8 which will be referred to as time-gates (tg) hereinafter. The time-gate is defined as an interval $[a,b) \subset [t_0, \infty)$, where a and b are predefined constants. Therefore one can consider a complete TPSF as being constructed from many individual time-gate signals. The actual time points that define the beginning and the end of a time-gate are preferably determined relative to the time, $t_o$, at which the light pulse is injected into the object. By detecting the signal of sequential time-gates using time gated detection techniques and cameras such as, but not limited to, a time-gated intensified charge coupled device (ICCD), it is possible to acquire the complete TPSF. However, acquisition of a complete TPSF in this manner requires long acquisition times which will be proportional to the number of time-gates acquired. In one aspect of the present invention the image may be constructed by acquiring only certain time-gates. As a result the acquisition time is greatly reduced. Overlapping time-gates can be allowed if the forward model is capable of taking this into account.

The selection of the time-gates relative to $t_o$ that will be used to construct an image may be based on the characteristics of the object such as the thickness and the anticipated optical properties. In the absence of prior knowledge about the anticipated optical properties of the object, a practical approximation to the complete TPSF could be obtained and be used for future selection of the time-gates.

In a preferred embodiment certain specific time gates or time points (infinitely small time gates) of the TPSF at which TD data will be acquired can be selected based on the following approach:

Based on the physics of diffuse light propagation, it can be assumed that a noiseless TPSF is a continuous and infinitely differentiable function defined on $R^+$. Critical points of a function can be identified via zeros of this function's derivative. Due to the fact that a TPSF has a characteristic shape (see 6 FIG. 1), the i-th derivative will yield a set of points where it became zero, which corresponds to extreme values of the underlying function. The first subset $s_1=\{s_{1,1}\}$ corresponding to the $1^{st}$ derivative describes the unique TPSF maximum. The second subset $s_2=\{s_{2,1}; s_{2,2}\}$ corresponding to the $2^{nd}$ derivative reveals two points where the curvature directionality changed. Derivatives of the higher order yield information on more subtle TPSF shape features. The subset $s_i$ corresponding to the i-th derivative can be defined as $s_i = \{s_{i,1}; \ldots; s_{i,i}\}$.

Given a TPSF f(t) represented with a set of M values (M>>n), e.g. $f=\{f(t_1), f(t_2), \ldots, f(t_M)\}$, $t_1 \geq a$, $t_M \leq b$, one can perform recursive numerical "differentiation" of the TPSF and of its' resulting "derivatives" by computing the quotient:

$$Q_i = \frac{f(t_{i+1}) - f(t_{i-1})}{t_{i+1} - t_{i-1}},$$

which would approximate the value of the derivative $f'(t_i)$.

Figure 6A:
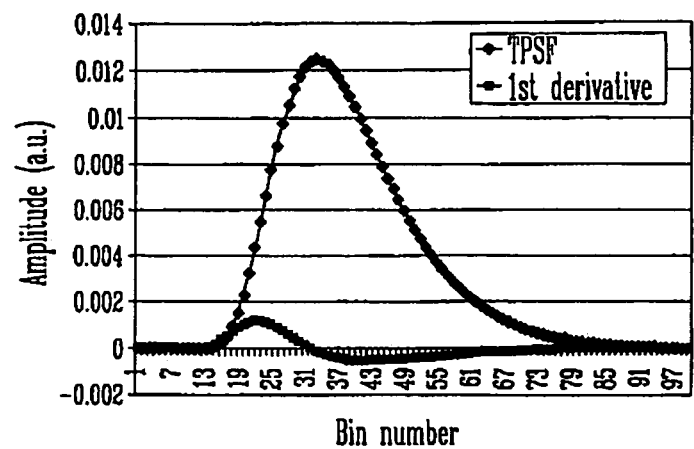
FIG. 6A is a plot of intensity over time in arbitrary units (i.e. a TPSF) along with a first derivative.
Figure 6B:
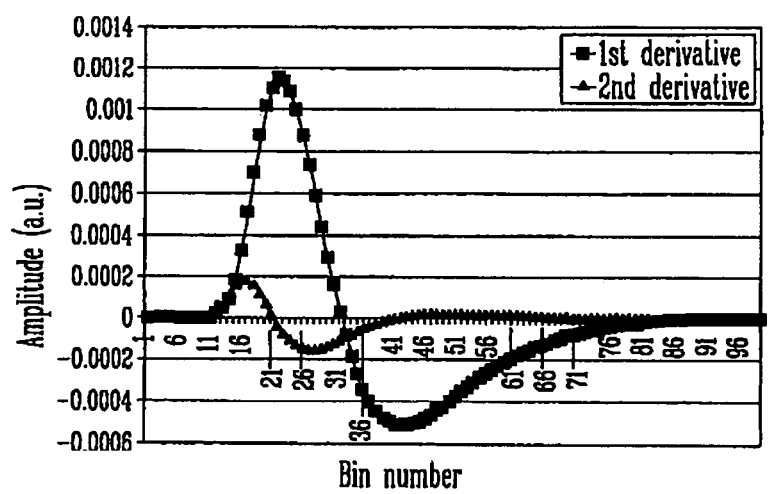
FIG. 6B is a plot of the first derivative of FIG. 6A along with a second derivative.

When plotted, characteristic sequence of functions will emerge as shown in FIGS. 6A and 6B. One observes that in this example $s_1=\{31.5\}$, $s_2=\{20.5; 40.5\}$, $s_3=\{14.5; 25.5; 48.5\}$, the values being the time point indices rather than absolute time.

In order to obtain an adequate TPSF representation with n points (or time gates), one would want to reflect the TPSF shape as fully as possible. The sequence $\{s_1; s_2; \ldots\}$ allows for identification of the most relevant points in the order of diminishing significance as the subset number increases. Note that elements within a given subset $s_i$ have equal significance with a noiseless TPSF. However, elements of $s_i$ may be ordered by assigning higher priority to elements that have higher $$\max_{k<i, l \leq k} |s_{i,j} - s_{k,l}|$$

in order to minimize the correlation of experimental errors.

One can consider $s_i$ the midpoints of a set of time-gates $s'_i$, i.e. $s'_i = \{\lfloor s_{i,1} - 0.5r_{i,1}, s_{i,1} + 0.5r_{i,1}\rfloor; \ldots; \lfloor s_{i,i} - 0.5r_{i,i}, s_{i,i} + 0.5_{i,i})\}$, where $r_{i,j}$ is the width of a respective time gate.

The procedure outlined above can yield $S^i = \{s_1^i; s_2^i; \ldots\}$, $i=1, \ldots, K$ for a given TPSF having index i. In order to reflect the most relevant features of a set of K TPSFs, one must arrive to $S_1 = s_1^1 \cup s_2^2 \cup \ldots \cup s_1^K$ first, to $S_2 = s_2^1 \cup s_2^2 \cup \ldots \cup s_2^K$ second and so on. The set $\{S_1; S_2; \ldots\}$ provides a sequence whose n starting elements should be used to represent the set of TPSFs in an optimal manner.

As mentioned above, $s_m^i$ might be replaced with a set of intervals in order to analyze time-gates instead of time points.

In a preferred embodiment of the invention the steps to select the appropriate time gates are as follows:

Acquire practical approximations to the complete TPSFs for all source-detector pairs that are capable of functioning simultaneously. At least one typical source position through the bulk medium should be used. The robustness of the subsequent analysis increases, as more typical source positions are included.

Approximate all measured TPSFs either based on a relatively simple model of photon propagation, e.g. assuming that propagation took place in a homogeneous medium, or interpolate the measured TPSFs to ensure the continuity and differentiability of the result.

Perform analysis yielding the set $\{S_1; S_2, \ldots\}$ as described above in order to determine the optimal n time-gates.

Acquire data with the determined n time-gates. n is an input parameter. In practice it can be determined via estimation of the resulting data set size that can be utilized to reconstruct images within a desired time frame.

Temporal resolution $r_0$, i.e. the minimal distance between $t_i$ and $t_{i+1}$, that yields virtually "uncorrelated" values $f(t_i)$ and $f(t_{i+1})$, is determined by the limitations of the data acquisition hardware and is, therefore, an input parameter. It is preferable to perform initial data acquisition with time-gate width and time steps of not more than $0.5 \times r_0$. Eventual width $r_i \geq r_0$ of the time-gate having index i is automatically chosen to ensure capturing the most relevant TPSF features revealed by the analysis.

The above described method for selecting time gates may be used in the context of a broader process for selecting appropriate time-gates when imaging a particular object. In one embodiment this broader process may comprise the use of banks of TPSF's obtained from a plurality of objects having given recorded characteristics and for which the derivative method described above has been applied to select appropriate time-gates. Thus, the selection of appropriate time-gates for a new object being imaged may then be made by matching certain predetermined characteristics of the object with those recorded in the data banks. When a "good" match has been found the time-gates that have been identified for the corresponding object in the data bank are used to acquire the TPSF of the object being imaged. For example, in the case of breast imaging, TPSF's can be acquired from a plurality of patients having different characteristics that can be recorded such as age, breast density, disease state etc. The derivative method is then applied to these TPSF's to select appropriate time-gates and the identity of the time-gates are associated with each patient. When it is desired to image the breast of a new patient the appropriate time-gates may be selected by simply matching the characteristics of this patient with those in the data bank thereby effecting the selection of the time-gates. It will be appreciated that the characteristics used in the data bank maybe chosen to reflect their relevancy to optical imaging.

Figure 3:
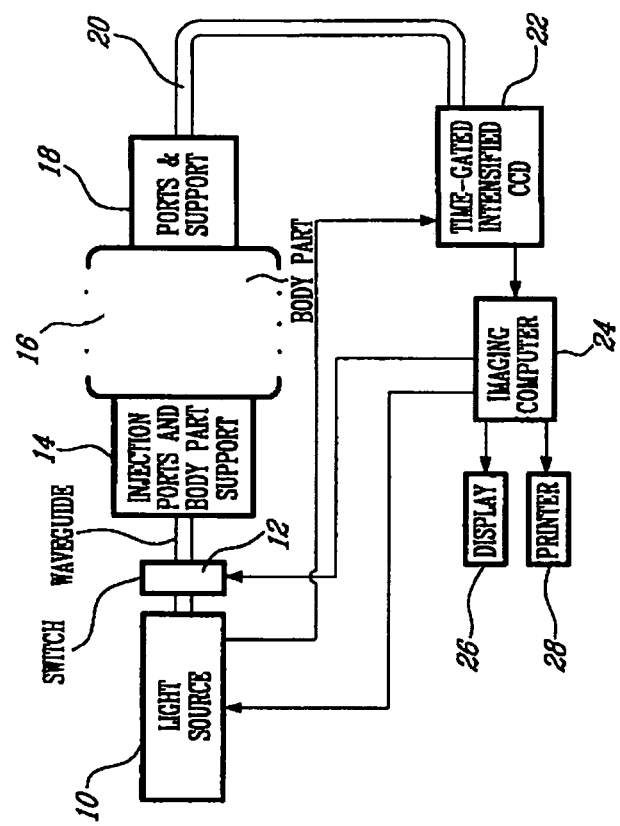
FIG. 3 is an example of a system that can be used to construct an optical image according to methods of the present invention.

An embodiment of the system that can be used to perform the data acquisition using the method of the present invention is schematically represented in FIG. 3. The pulsed light source 10 has an output optically coupled via a switch 12 to one or a plurality of injection ports 14 of a support. The injections port are preferably positioned at a number of fixed positions over the imaging area although the injection ports may alternatively be moveable over the body surface, provided that the body part 16 being imaged is immobilized. As is known in the art the injection and collection ports may directly contact the body or a coupling medium may be used between the body and the injection/collection ports. In FIG. 3, the collection ports 18 and support are arranged in transmission mode for breast imaging. However, it is also possible to have an injection ports/object/collection ports geometry such that the collection ports are on the same surface as the injection ports. The light source may be a polychromatic source or a monochromatic source such as a laser. The pulses preferably have a duration of about 1 to 100 picoseconds and an average power of 100 mW.

The collected optical signals may be communicated by one or more waveguides 20 such as 400/440 micron graded index multimode optical fibers to one or more detection positions of a time gated detector 22 such as a gated ICCD camera, for example a PicoStar™ camera by LaVision.

A large number of pulses may be injected and their corresponding camera signals detected and processed by imaging computer 24 to determine the value of at least one time gate and, in the case of simultaneous detection, two or more selected time gates of a TPSF. Such data are gathered for a sufficiently large number of detecting port positions to ensure robust reconstruction of an image of the object. The resulting image can be displayed on a monitor 26 or a hard copy can be obtained at 28.

It will be appreciated that the relative positions of the injectors and detectors may be modified as needed to optimize the quality of the image. Thus different geometries of the injection ports/collection ports/object assembly may be used, for example by placing collection ports either proximally or distally or a combination of both, depending on several factors such as, the thickness of the object, the nature of the medium comprising the object. The value for each pixel or voxel of an image generated from the data collected according to the present invention will benefit from a plurality of source detector locations with respect to the position of the pixel or voxel, as well as a plurality of time-gates.

In an aspect of the present invention the acquisition time can be further reduced by simultaneously detecting a desired number of time-gates of one or more TPSF's. This can be achieved by collecting the light signal exiting from the OOI at several (m) locations. Temporal delays are then introduced in the propagation of these optical signals such that the m TPSF's reach the time-gated detector in a staggered manner. Therefore, using a time-gated camera, it is possible to simultaneously detect m different time-gates of the TPSF's.

Figure 4:
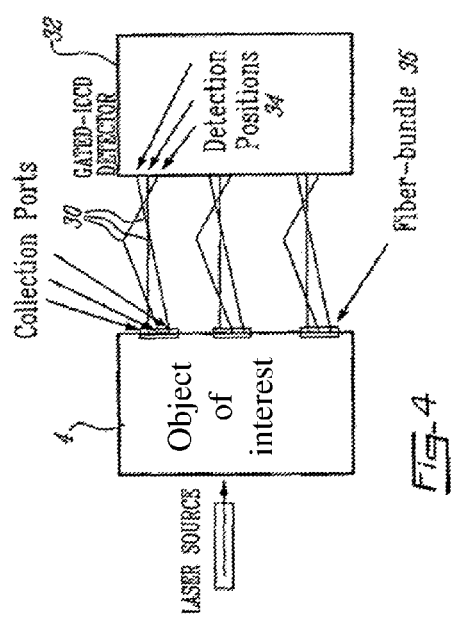
FIG. 4 is a schematic representation of an embodiment of the system used to simultaneously detect two or more time-gates.
Figure 5:
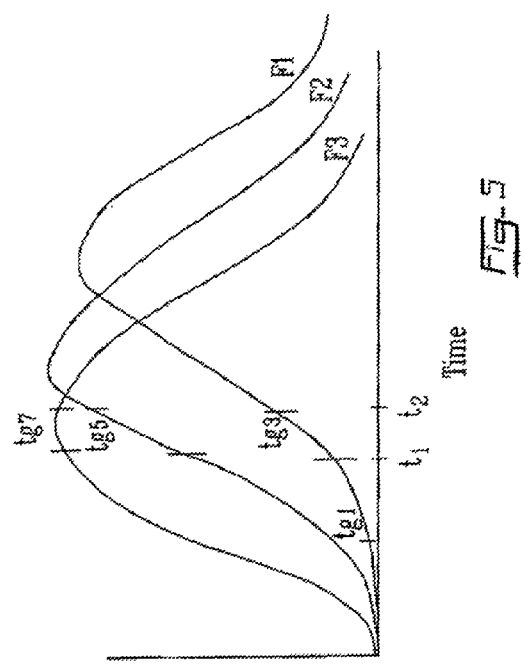
FIG. 5 is a graphical representation of three staggered TPSF's.

This embodiment of the invention will be better understood with reference to FIGS. 4 and 5. In FIG. 4 a schematic diagram of a possible arrangement of a system used to simultaneously detect m time gates is depicted. In this embodiment optical fibers 30 are used to collect and channel the light exiting the OOI 4 to a time-gated detector 32. The fibers are of different lengths and therefore the time required for the optical signal to travel from the collecting point to the detection point at the detector is different for each fiber thus introducing delays in the propagation of the optical signal. Each fiber, or bundle of fibers, is coupled to a different detection position 34 at the detector. Consequently, the time required for a particular time gate, tg, to reach the detection position in the detector will depend on the length of the fiber through which it is propagated. FIG. 5 is a graphic representation of three staggered TPSF's propagated by three different optical fibers F1, F2, and F3 having different lengths with length of F1>length of F2>length of F3. It can be appreciated that a given time-gate, say tg3, reaches the detector at a different time depending on whether it is propagated by F1, F2 or F3. Now if the detector is time-gated to detect only the signal during the interval defined by t1 and t2, different time-gates will be detected for each fiber. In our example tg3, tg5, and tg7 are simultaneously detected. It can be seen that the number of time gates that can be detected simultaneously is equal to the number of fibers. The fibers can be bundled within a defined area of a given detector and provide the desired time-gates simultaneously with one 'snapshot' of the time-gated camera. This leads to a decrease in the acquisition time by a factor of approximately n compared to serially acquired time-gates.

It will be appreciated that the length of the fibers can be selected to detect the desired time gates (or the desired sections of the TPSF). To refer to our example, if one wanted to simultaneously detect tg7, tg5 and tg1, the length of F1 could be increased accordingly. However, it will also be appreciated that the simultaneous detection of the desired time-gates can be effected by directing each fiber to a different detector and by adjusting the time gate of each detector so as to detect one of the desired time gate. Typically, an increase of 11 cm in fiber length will induce a time delay of about 500 ps.

The delays in the propagation of the optical signals may also be introduced by using variable delay optical waveguides that are well known in the art.

It will be appreciated that the signal to noise ratio (SNR) may limit the number of fibers and thus the number of time gates that can be simultaneously detected. In practice, it is a decision between how many detector positions are required, the number of time-gates simultaneously required and the total number of fibers which can be packed onto the gated camera. Referring back to FIG. 4, it will be further appreciated that if the fibers or the fiber bundles 35 are sufficiently close together, the TPSF's may be substantially identical.

The embodiment(s) of the invention described above is (are) intended to be exemplary only. The scope of the invention is therefore intended to be limited solely by the scope of the appended claims.

I claim:

1. A method for optical imaging of a light scattering object, the method comprising steps of:
   i) selecting a plurality of time-gates for imaging the object;
   ii) injecting a pulse of light at an injection port into said object at time t;
   iii) collecting light from said object at a plurality of collection ports at the selected plurality of time-gates to provide a plurality of optical signal based temporal point spread function and collecting light only for selected time gates, and not for a series of consecutive time-gates; and
   iv) introducing corresponding temporal delay to each one of the optical signal based temporal point spread functions for obtaining staggered optical based temporal spread point spread functions;
   wherein said light collection of said time-gated signals at said selected plurality of time-gates comprises:
      obtaining at least a first derivative of each temporal point spread function; and
      identifying one or more time intervals of each temporal point spread function in which a first derivative is zero at a point in said time interval thereby effecting said collection of said time-gated signals.

2. The method as claimed in claim 1 wherein said plurality of collection ports are adjacent to one another and said temporal point spread functions are identical.

3. The method as claimed in claim 2 wherein said time-gated signals span a time interval defined by an initial time and a final time which are set relative to $t_o$.

4. The method as claimed in claim 3 wherein said light collection is performed for a plurality of injection port/object/detector port geometries.

5. The method as claimed in claim 4 wherein said collection is based on one or more optical properties of said object.

6. The method as claimed in claim 4 wherein said initial time and said time-gated signals are estimated based on one or more optical properties of said object that influence propagation of said light within said object.

7. The method according to claim 6 wherein said one or more properties comprise thickness of said object.

8. The method as claimed in claim 1 wherein said time-gated signals are further selected based on an order of said derivative.

9. The method as claimed in claim 1 wherein said collection of said time-gated signals comprises:
   i) retrievably storing said time-gated signals such that said time-gated signals are associated with at least one predetermined characteristic of a corresponding object; and
   ii) matching a characteristic of a new object to be imaged with said stored predetermined characteristics to identify corresponding time-gates to be used in imaging said new object.

10. The method as claimed in claim 1 wherein said step of light collection is performed using a time-gated detector.

11. The method as claimed in claim 10 wherein the time-gated detector is an intensified charge-coupled device (ICCD) camera.

12. The method as claimed in claim 1 wherein the two or more time-gated signals are simultaneously detected at two or more time-gated detectors having a synchronized acquisition time gate.

13. The method as claimed in claim 12 wherein the step of simultaneously detecting comprises detecting said selected time-gates using a time-gated detector comprising a 2-dimensional array of pixels.

14. The method as claimed in claim 13 wherein the time-gated detector is an ICCD camera.

15. The method as claimed in claim 1 wherein the collecting of the light is achieved by providing one or more optical fibers.

16. The method as claimed in claim 15 further comprising adjusting a relative length of fibers to introduce the relative temporal delay.

17. The method as claimed in claim 16 wherein the fibers are grouped together into one or more bundles.

18. The method according to claim 17 wherein each fiber in the one or more bundles is directed to a distinct detection position of the time-gated detector or to a distinct time-gated detector.

19. The method as claimed in claim 18 wherein the one or more bundles are spatially localized such as to collect light from one or more desired areas of said object.

20. The method as claimed in claim 19 wherein the one or more bundles are coupled to one or more time-gated detectors.

21. A system for optical imaging of a light scattering object the system comprising:
   i) at least one light injection port and
   ii) a light collecting apparatus comprising a plurality of collection ports and providing a plurality of sequential time gated optical signal based temporal point spread functions; and said light collecting apparatus collects light at a selected plurality of time-gates and not for a series of consecutive time-gates
   wherein said light collection apparatus collects light from an object at the plurality of collection ports and collects light of said time-gated signals at said selected plurality of times-gates by:
      obtaining at least a first derivative of each temporal point spread function; and
      identifying one or more time intervals of each temporal point spread function in which a first derivative is zero at a point in said time interval thereby effecting said collection of said time-gated signals.

22. The system according to claim 21 wherein the collection ports are adjacent to one another.

23. The system as claimed in claim 22 wherein the light collecting apparatus comprises one or more optical fibers.

24. The system as claimed in claim 23 wherein the optical delay feature comprises a difference in the relative length of the optical fibers.

\* \* \* \* \*